United States Patent [19]
Ellias

[11] Patent Number: 5,868,141
[45] Date of Patent: Feb. 9, 1999

[54] ENDOSCOPIC STOMACH INSERT FOR TREATING OBESITY AND METHOD FOR USE

[76] Inventor: Yakub A. Ellias, 2272 Renshaw Ave., Dayton, Ohio 45439

[21] Appl. No.: 855,966

[22] Filed: May 14, 1997

[51] Int. Cl.[6] .................................................. A61B 17/00
[52] U.S. Cl. ........................... 128/898; 128/899; 604/909
[58] Field of Search .................................. 606/191, 194, 606/195, 198, 200, 1; 128/898, 899; 604/909

[56] References Cited

U.S. PATENT DOCUMENTS

| | | | |
|---|---|---|---|
| 3,540,431 | 11/1970 | Mobin-Uddin | 606/200 |
| 4,133,315 | 1/1979 | Berman et al. . | |
| 4,416,267 | 11/1983 | Garren et al. . | |
| 4,592,339 | 6/1986 | Kuzmak et al. . | |
| 4,607,618 | 8/1986 | Angelchik . | |
| 4,823,808 | 4/1989 | Clegg et al. . | |
| 4,899,747 | 2/1990 | Garren et al. . | |
| 5,010,894 | 4/1991 | Edhag | 607/128 |
| 5,108,418 | 4/1992 | Lefebvre | 606/200 |
| 5,234,454 | 8/1993 | Bangs . | |
| 5,306,300 | 4/1994 | Berry . | |
| 5,423,872 | 6/1995 | Cigaina . | |
| 5,424,463 | 6/1995 | Lardy et al. . | |

OTHER PUBLICATIONS

Abstract of Article by J.S. Cheah, Entitled "Current Management of Obesity", Singapore Medical Journal, Jun. 1996.

Abstract of Article by D.J. Goldstein, et al. Entitled "Long-term Weight Loss; The Effect of Pharmacologic Agents", American Journal of Clinical Nutrition, Nov. 1994.

Abstract of Article by R. Wolfel, et al. Entitled "Weight Reduction After Gastric Bypass and Horizontal Gastroplasty for Morbid Obesity", European Journal of Surgery, Apr. 1994.

Abstract of Articles by G. Stoa–Birketvedt Entitled "*Effect of Cimetidine Suspension on Appetite and Weight in Overweight Subjects*", BMJ. 306 (6885) :1091–3, Apr. 1993.

Abstract of Article by R.E. Andersen, et al. Entitled "Relation of Weight Loss to Changes in Serum Lipids and Lipoproteins in Obese Women", American Journal of Clinical Nutrition, Aug. 1995.

Abstract of Article by T.H. Brown, et al. Entitled "The Effect of an Intragastric Balloon on Weight Loss, Gastric Acid Secretion, and Serum Peptide Levels", Am. Surg., Feb. 1988.

Abstract of Aricle by K.D. Lindor, et al. Entitled "Intragastric Balloons in Comparison with Standard Therapy for Obesity — a Randomized, Double–Blind Therapy", Mayo Clin. Proc.Nov. 1987.

Abstract of Article by C.S. Wayman, et al. Entitled The Role of Endoscopy After Vertical Banded Gastroplasty, Gastrointest. Endosc., Jan.–Feb. 1992.

Abstract of Article by R.B. Hogan, et al. Entitled "A Double–Blind, Randomized, Sham–Controlled Trial of the Gastric Bubble for Obesity", Gastrointest. Endosc., Sep.–Oct. 1989.

Abstract of Article by S.B. Benjamin Entitled "Small Bowel Obstruction and the Garren–Edwards Gastric Bubble: An Iatrogenic Bezoar", Gastrointest. Endosc., Nov.–Dec. 1988.

Article by Peter J. Carek et al. Entitled "Management of Obesity: Medical Treatment Options", American Family Physician, Feb. 1, 1997.

Primary Examiner—William Lewis
Attorney, Agent, or Firm—Thompson Hine & Flory LLP

[57] ABSTRACT

An endoscopic stomach insert for treating obesity in humans by reducing the desire for eating, comprising a base-sized for passing through a human mouth and esophagus; a plurality of flexible blades coupled at one end thereof to the base and circumferentially arranged about the base central axis, where the blades are biased to extend substantially radially outward and downward from the base; and a retainer for releasably coupling the distal portions of the blades within close proximity to each other about the central axis of the base. The insert is thus adapted to be passed through the mouth and esophagus and into a human stomach, and upon releasing the retainer within the stomach, the blades are biased to flare outwardly into the form of a dome-shaped cage, applying pressure to the stomach, and thus causing a sensation of fullness within the stomach and reducing the desire for eating.

14 Claims, 7 Drawing Sheets

ENDOSCOPIC STOMACH INSERT FOR TREATING OBESITY AND METHOD FOR USE

BACKGROUND

The present invention is an apparatus and method for treating obesity in humans, and particularly, a device for endoscopic insertion into the stomach of a human to cause a reduced desire for eating.

Obesity is arguably one of the most serious health problems in the United States, afflicting over 60 million people of all ages. Apart from physical and psychological effects, especially on the younger population, obesity predisposes to serious diseases such as coronary artery disease, hyperlipidemia, hypertension, and diabetes mellitus. The costs to the health system is a staggering $39 billion per year.

Weight reduction can be achieved either by increasing caloric expenditure through exercise and/or by reducing caloric intake. Reduced caloric intake can be achieved in a number of ways; surgical procedures to reduce the stomach capacity or increase the food transit time in the gastrointestinal tract, appetite suppressants like amphetamines or noradrenargic compounds, or other methods such as introducing balloons into the stomach. Surgical procedures to reduce the stomach capacity or increase food transit time in the gastrointestinal tract carry with them the risk of surgery as well as post-operative complications. The appetite suppressants act on the central nervous system and are associated with considerable morbidity and side effects. Balloon inserts have several disadvantages, which include failure due to bursting or dislodging, intestinal obstruction (blockage of the intestinal lumen), and the requirement of complicated devices and/or procedures to secure the balloons within the stomach.

Accordingly, there is a need for a non-surgical stomach insert that is easily inserted and/or removed from the stomach, that does not have the tendency to dislodge into the distal intestinal tract and cause obstruction, and that does not significantly obstruct the gastric lumen.

The present invention is an endoscopic stomach insert for treating obesity in humans by reducing the desire for eating, comprising a base-sized for passing through a human mouth and esophagus; a plurality of flexible spokes coupled at one end thereof to the base and circumferentially arranged about the base central axis, where the spokes are biased to extend substantially radially outward from the base; and a retainer for releasably coupling the distal portions of the spokes within close proximity to each other about the central axis of the base. The apparatus is thus adapted to be passed through the mouth and esophagus and into a human stomach, and upon releasing the retainer within the stomach, the spokes are biased to flare outwardly and apply pressure to the stomach, thus causing a sensation of fullness within the stomach and reducing the desire for eating.

In a preferred embodiment, the endoscopic stomach insert comprises a disc having a diameter sized for passing through a human mouth and esophagus, where the disc includes a guide-hole extending axially therethrough for receiving a guide-wire; at least three flexible plastic blades, each of the blades being substantially flat and curved with respect to the longitudinal axis and having a substantially blunt distal end, and each of the blades being coupled at its proximate end to the disc, such that its concave surface faces downwardly or inwardly with respect to the central axis of the disc; a retainer for coupling the blades within close proximity to each other about the lower end of the disc and about the central axis of the disc; and a projection extending from the upper surface of the disc.

Each blade also includes an eyelet extending from its concave surface at a point approximately one-quarter of the way from its proximate end. And the retainer is preferably a severable elastic band extending through each of the eyelets.

The blades are circumferentially arranged about the center axis of the disc and are biased to extend substantially radially outwardly and downwardly from the disc, such that when the blades are not retained together by the elastic band, they tend to fan out to form a cup-shaped or dome-shaped cage or skeleton.

The disc is adapted to ride on a guide-wire extending into a human mouth and esophagus and into the stomach, such that the insert can be deposited within the stomach. Upon severing the elastic band within the stomach, the blades will be biased to flare outwardly such that the convex surfaces of the blades will apply pressure to the stomach, thus causing a sensation of fullness within the stomach and reducing the desire for eating.

The projection extending from the upper surface of the disc provides means for gripping the insert with an endoscopic instrument (i.e. forceps) such that the insert can be extracted back out from the stomach, through the esophagus, and out through the mouth.

The endoscopic procedure for treating obesity using the above insert comprises the steps of: endoscopically extending a guide-wire into a patient's mouth, through the patient's esophagus, and into the patient's stomach; guiding the endoscopic stomach insert along the guide-wire, into the patient's mouth, through the patient's esophagus, and into the patient's stomach; endoscopically releasing the retainer such that the spokes or blades will flare outwardly and apply pressure to the stomach, thus causing the patient to experience a sensation of fullness within the stomach and reducing the patient's desire for eating.

Accordingly, it is an object of the present invention to provide an endoscopic stomach insert and method for the non-surgical treatment of obesity; it is a further object of the present invention to provide an endoscopic stomach insert that does not substantially obstruct the passage of food through the gastric lumen; it is a further object of the present invention to provide an endoscopic stomach insert that does not have the tendency to dislodge from the stomach and thus subsequently lodge into the distal intestinal tract, causing an obstruction; and it is also an object of the present invention to provide an endoscopic insert that is easily removed from the stomach once the patient's desired weight-loss has been achieved.

These and other objects and advantages of the present invention will be apparent from the following description, the accompanying drawings, and the appended claims.

DETAILED DESCRIPTION

Figure 1:
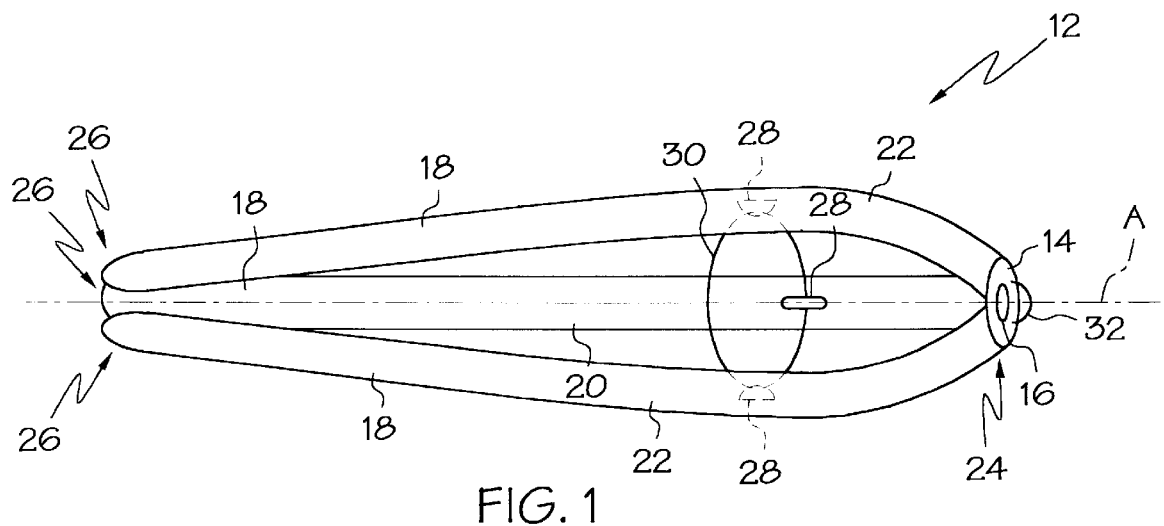
FIG. 1 is a perspective, elevational, longitudinal side view of a preferred embodiment of the present invention shown in closed form.
Figure 2:
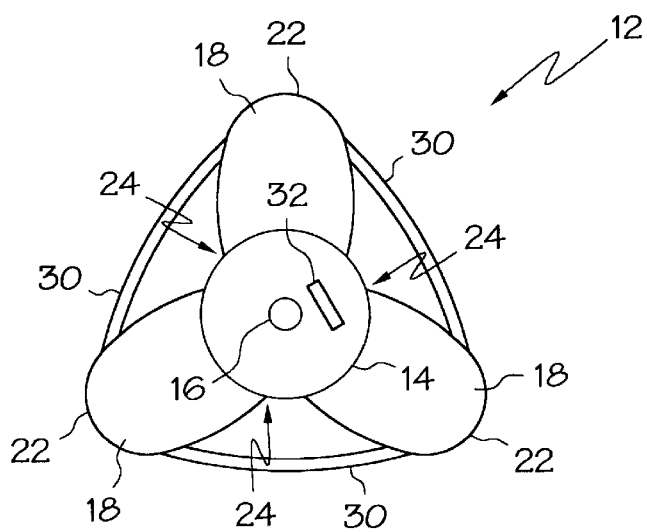
FIG. 2 is a perspective elevational, end-on view of the preferred embodiment of the present invention shown in closed form.
Figure 3A:
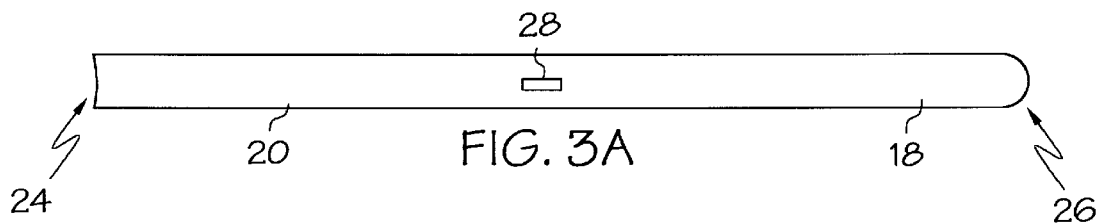
FIGS. 3A–3C are perspective longitudinal top, tilted, and side views, respectively, of the concave surface of a blade component of the present invention.
Figure 3B:
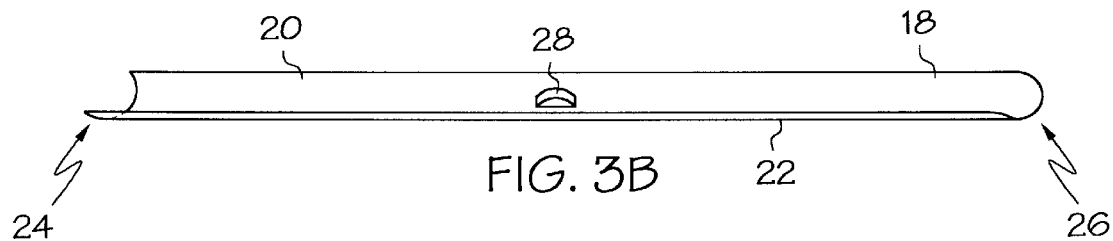
Figure 3C:
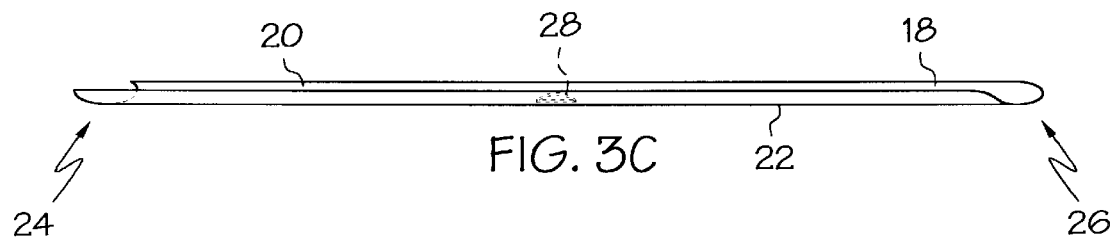

As shown in FIGS. 1 and 2, a preferred embodiment of the endoscopic stomach insert of the present invention, designated as 12, includes a disc 14 having a diameter sized for passing through a human mouth and esophagus. The disc has a central axis A and a guide-hole 16 extending axially therethrough for receiving a guide-wire as will be described below. The endoscopic stomach insert also includes at least three flexible plastic blades 18.

As shown in FIGS. 1, 2 and 3A–3C, the blades 18 are substantially flat and curved with respect to their longitudinal axis, thus providing each of the blades with a concave surface 20 and a convex surface 22. The blades are each pivotally coupled to the disc 14 at their proximate ends 24, i.e., by hinges, such that the concave surfaces 20 of the blades each face inwardly towards the central axis A of the disc. The distal end 26 of each blade is preferably rounded or blunted to reduce any propensity of causing discomfort to the stomach lining when inserted within the stomach. Optionally, a cushioning or blunted component can be attached to the distal end 26 of each blade to further avoid discomfort to the patient's stomach when inserted therewithin.

In the preferred embodiment, each of the blades also include an eyelet 28 or d-ring attached to and extending from the concave surface 20 of the blade. Each eyelet 28 is preferably diametrically aligned with the axis A, and is positioned between the distal end 26 and proximate end 24 of the blade, preferably closer to the proximate end. A severable elastic band 30 extends through each of the eyelets 28 and thus retains the blades 18 in close proximity to each other about the central axis A of the disc 14. The insert 12, with the blades 18 retained in such a manner is referred to as being in its "closed" position. When in the closed position, the blades tend to form the shape of an asymmetrical, elliptical cage.

Figure 4:
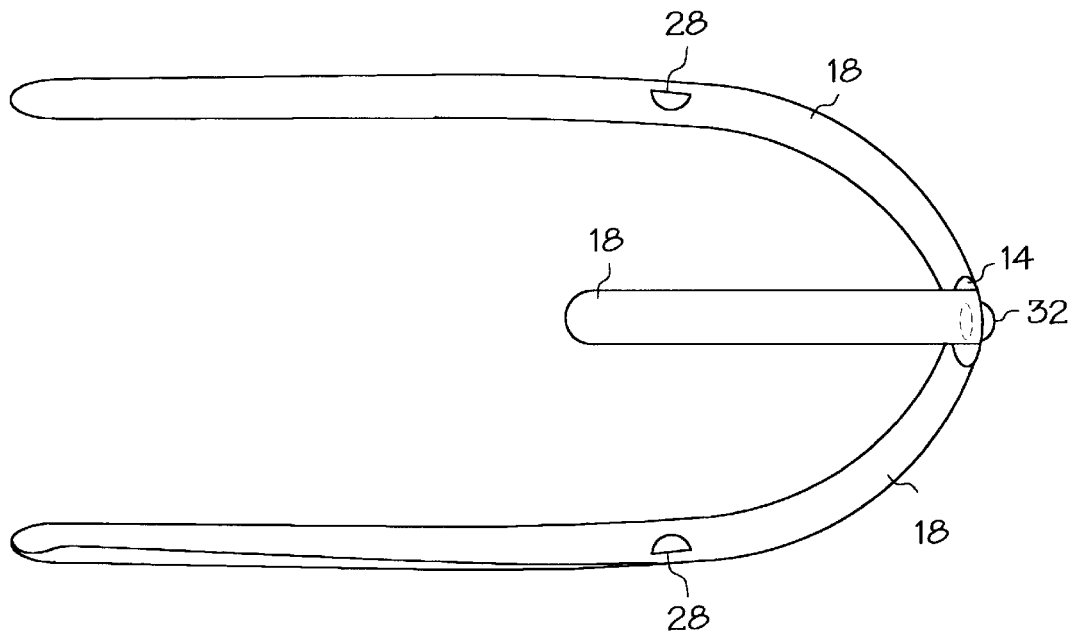
FIG. 4 is a perspective view of a preferred embodiment of the present invention shown in open form.

As shown in FIG. 4, each of the blades 18 are biased such that, when the elastic band 30 is not present to retain the blades together in close proximity about the central axis A of the disc, i.e., when the insert 12 is in its "open" position, the blades 18 tend to flare outwardly and downwardly from the disc 14 thus forming a substantially cup-shaped or dome-shaped skeleton or cage.

The operable length of each of the blades can range from approximately 6 centimeters to approximately 14 centimeters, and in the preferred embodiment the length of each blade is approximately 10 centimeters. The preferred length of the asymmetrical elliptical cage of the insert in the closed position is approximately 10 centimeters long. The widest diameter of the elliptical cage is preferably situated approximately 2.5 centimeters distally from the disc 14; and the widest diameter of the cage can range from approximately 1 centimeter to 2 centimeters, and is preferably approximately 1.5 centimeters. The operable diameter of the disc can range from 6 millimeters to 10 millimeters, and in the preferred embodiment is 8 millimeters in diameter, and the guidehole 16 is preferably 4 millimeters in diameter. In the preferred embodiment, the eyelets 28 are positioned approximately 2 centimeters from the proximate ends 24 of the blades 18, where each of the eyelets has a radius of approximately 0.125 centimeters.

Extending from the top surface of the disc 16 is a projection or ring 32. As will be described below, this ring 32 provides for the gripping of the insert 12 with an endoscopic forcep instrument, thus enabling the insert 12 to be easily removed from the stomach by an endoscopic procedure.

Figure 5:
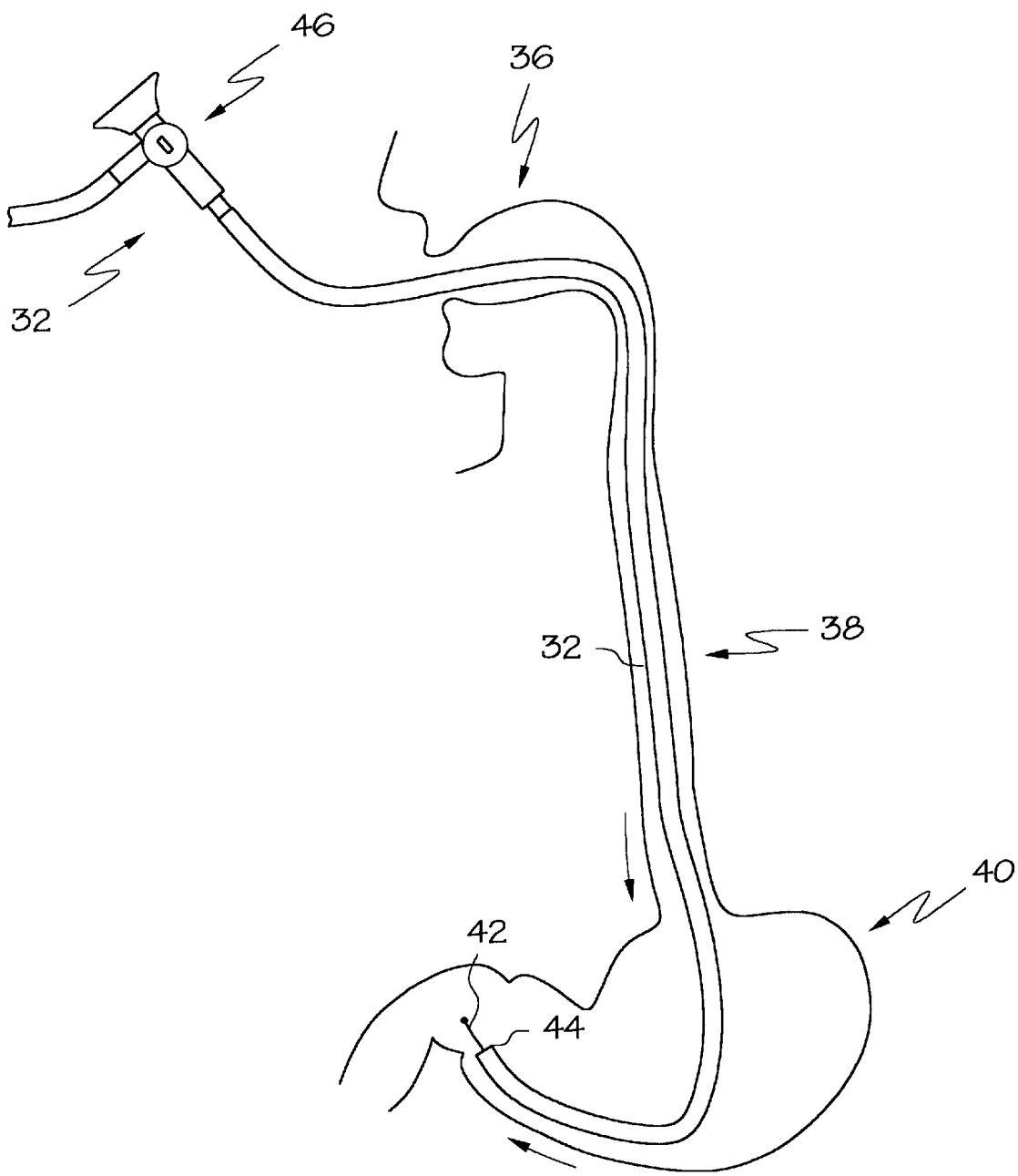
FIG. 5 is a representation of a patient's mouth, esophagus and stomach, showing an endoscope inserted therein in accordance with the insertion method of the present invention.

A method for endoscopically inserting the stomach insert 12 into a stomach of a patient is as follows. As shown in FIG. 5, a fiber optic endoscope 32 is inserted through a patient's mouth 36, esophagus 38 and into a patient's stomach 40. A guide-wire 42 is then inserted into and through the endoscope, into the patient's stomach. Once the guide-wire is inserted, the endoscope 32 is removed, leaving the guide-wire in the patient's stomach. A suitable endoscope for use with the present invention is an Olympus GIF-XQ140 Endoscope commercially available from Olympus Corp., Chicago Ill. Typical endoscopes for use with the present invention preferably include a means, such as a fiber bundle mounted in a flexible tube, to carry light into the visual field and to carry an undistorted image back to the examiner's eye. The endoscope also contains wire controls for integrated multi-directional movement of the tip 44 at least 180° in either direction. One or more separate channels are also typically available in the endoscope for suction or for passage of diagnostic instruments such as biopsy forceps, cytology brushes, cutters, catheters etc. Control of the various accessories, tip control, and an air-water insufflation can be typically found in the control handle 46.

Figure 6:
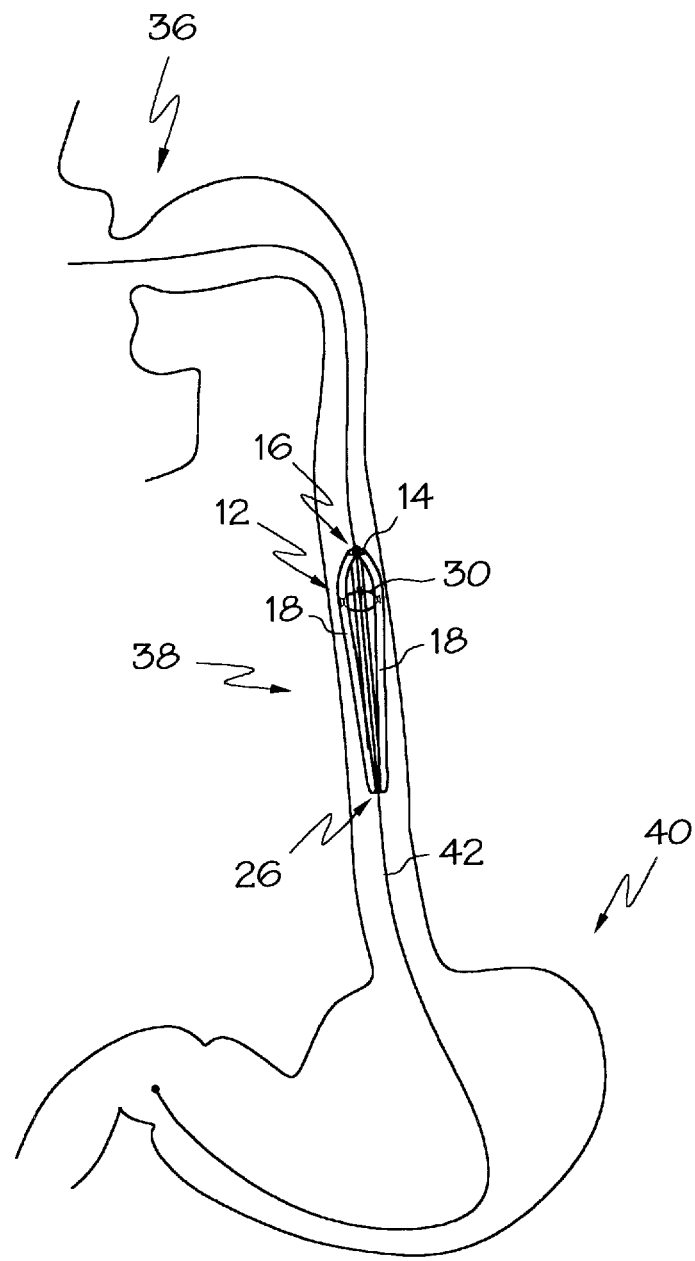
FIG. 6 shows the endoscopic stomach insert of the present invention riding on a guide-wire extending through a patient's esophagus in accordance with the insertion method of the present invention.
Figure 7:
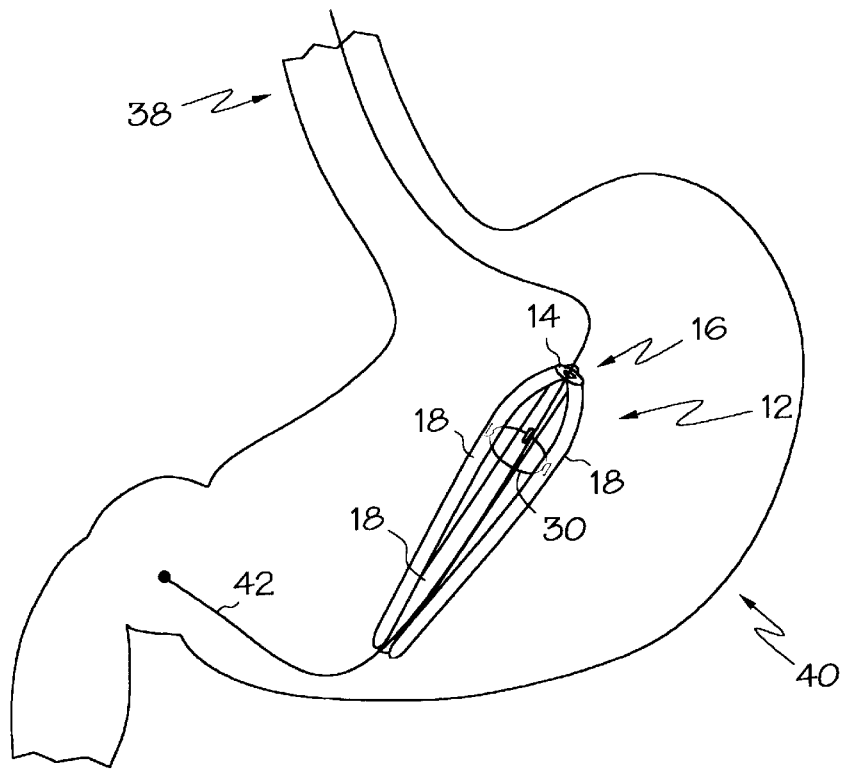
FIG. 7 is the insert of the present invention riding on a guide-wire and guided into a patient's stomach in accordance with the insertion method of the present invention.

As shown in FIG. 6, after the endoscope 32 has been removed, the insert 12 is positioned on the guide-wire 42 by threading the guide-wire 42 through the guide-hole 16 of the disc. As shown in FIG. 6, the instrument is inserted into the mouth 36 and esophagus 38 such that the proximate ends 26 of the flexible blades 18 enter first and such that the disc 14 enters last. Because the elastic band 30 retains the blades 18 substantially close to the central axis A of the disc to form an asymmetrical, elliptical cage having a diameter at its widest point of approximately 1.5 centimeters, the insert 12 is easily guided under endoscopic visualization through the patient's mouth 36 and esophagus 38 and into the patient's stomach as shown in FIG. 7. Once the insert 12 is positioned within the patient's stomach 40, the guide-wire 42 is then threaded (under endoscopic visualization) back through the insert 12 and through the guidehole 16 in the disc 14, and back out through the esophagus and mouth of the patient.

Figure 8:
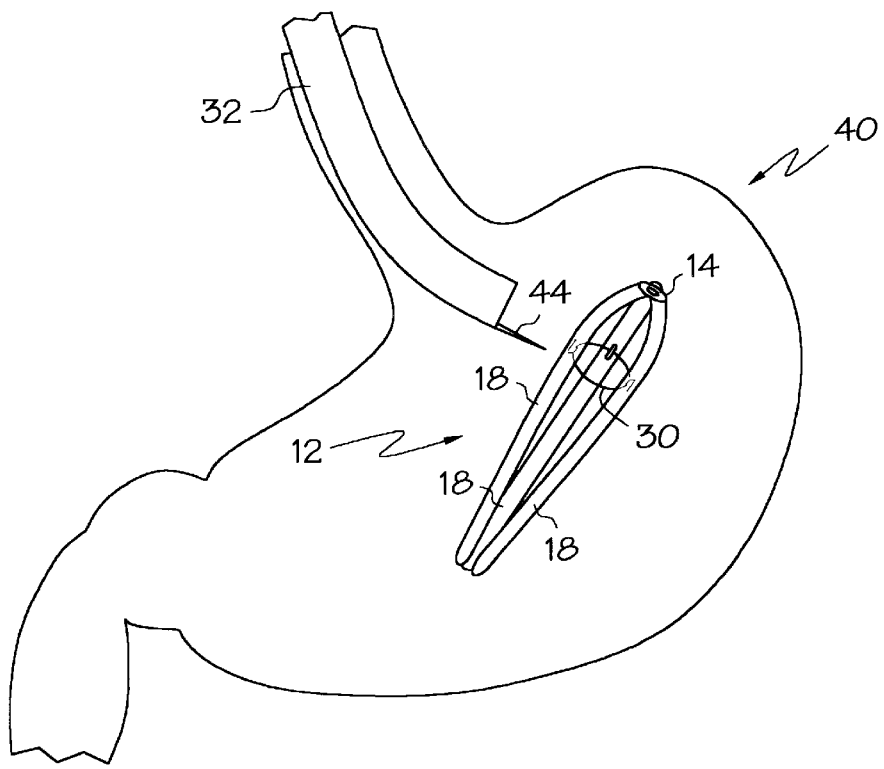
FIG. 8 shows the stomach insert of the present invention residing within the patient's stomach, and an endoscopic cutting tool positioned within the stomach for releasing the retainer component of the stomach insert in accordance with the insertion method of the present invention.

As shown in FIG. 8, a fiber optic endoscope 32 is then used to guide a cutting tool 44 into the stomach 40 such that the cutting tool 44, under endoscopic visualization, can be used to sever the elastic band 30 retaining the blades 18 of the insert in the closed position. An example cutting tool sufficient for use with the present invention is a KD-6G1Q/54430 sphincterotome, commercially available from Olympus Corp. The severed band 30 can then either be left in the stomach such that it will be passed from the intestinal tract, or later extracted using known endoscopic means.

Figure 9:
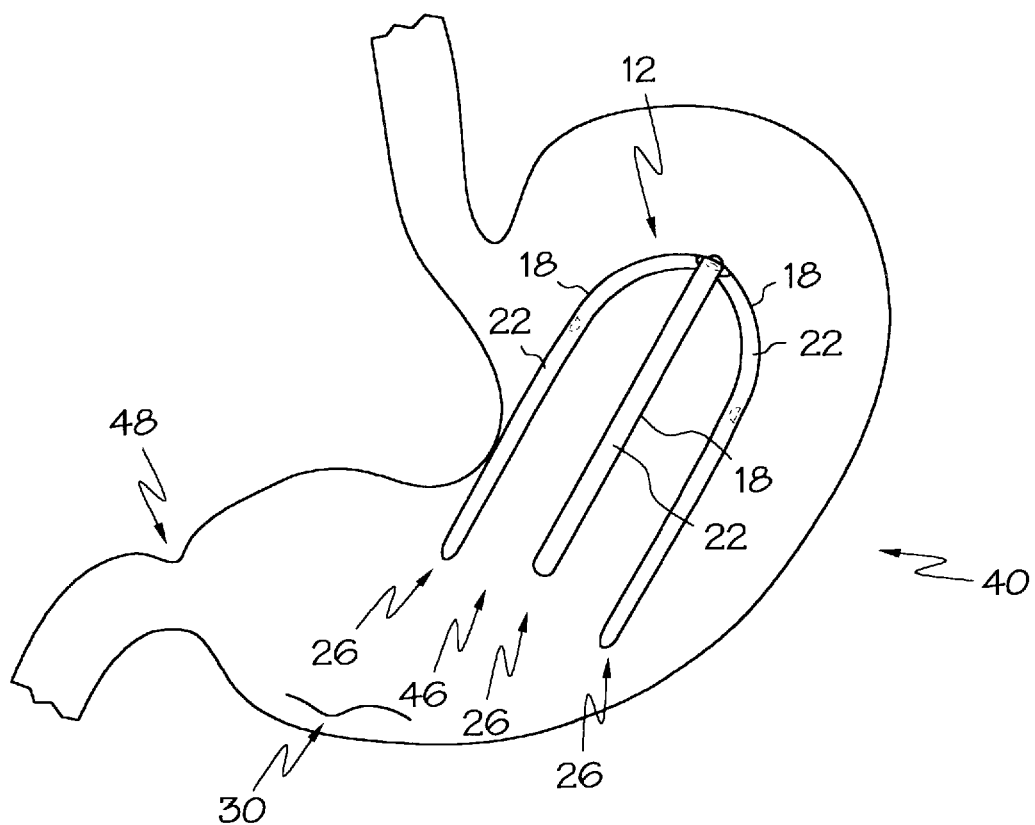
FIG. 9 shows the stomach insert residing in a patient's stomach in the open position in accordance with the insertion method of the present invention.

As shown in FIG. 9, once the elastic band 30 has been severed, the blades 18 are biased to fan out into their open position, thus forming a substantially cup-shaped or dome-shaped cage within the patient's stomach. The flaring out of the blades causes the convex surfaces 22 of the blades to apply pressure to the interior walls of the stomach, thus causing a sensation of fullness within the stomach, reducing the desire for eating. Because the insert 12 in its open form is substantially larger than the pyloric opening 48 leading to the intestinal tract, the insert 12 will be adequately retained within the stomach 40, without the risk of any blockage to the intestinal tract. Because the spaces are provided between the blades 18 of the insert in its open position, the insert 12 does not completely obstruct the gastric lumen, thus allowing food to pass freely therethrough. Finally, because of the blunted distal ends 26 of the blades, the patient does not experience significant discomfort or injury to stomach lining while the insert 12 is opened within the patient's stomach 40.

Figure 10:
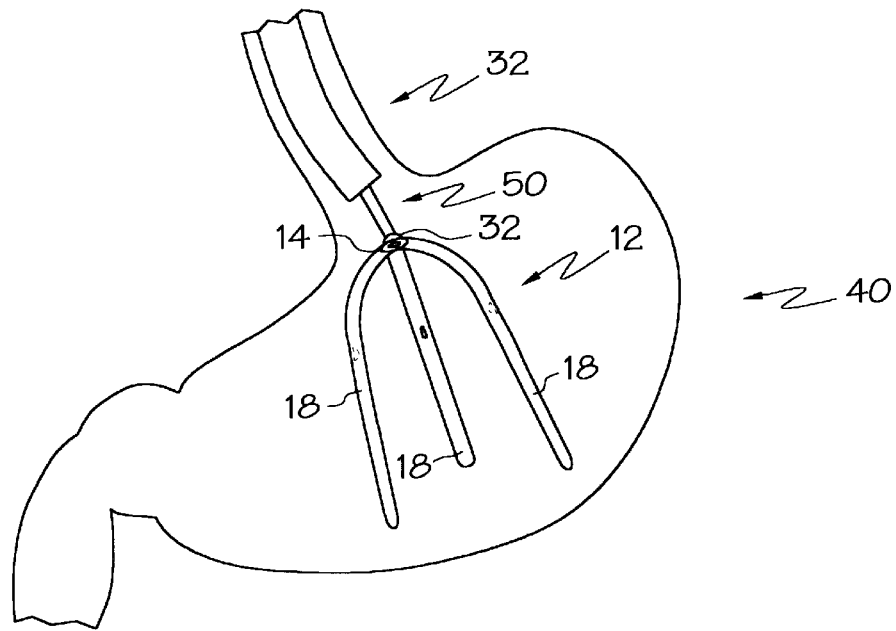
FIG. 10 shows the stomach insert residing in a patient's stomach and being gripped by an endoscopic forcep instrument in accordance with the extraction method of the present invention.
Figure 11:
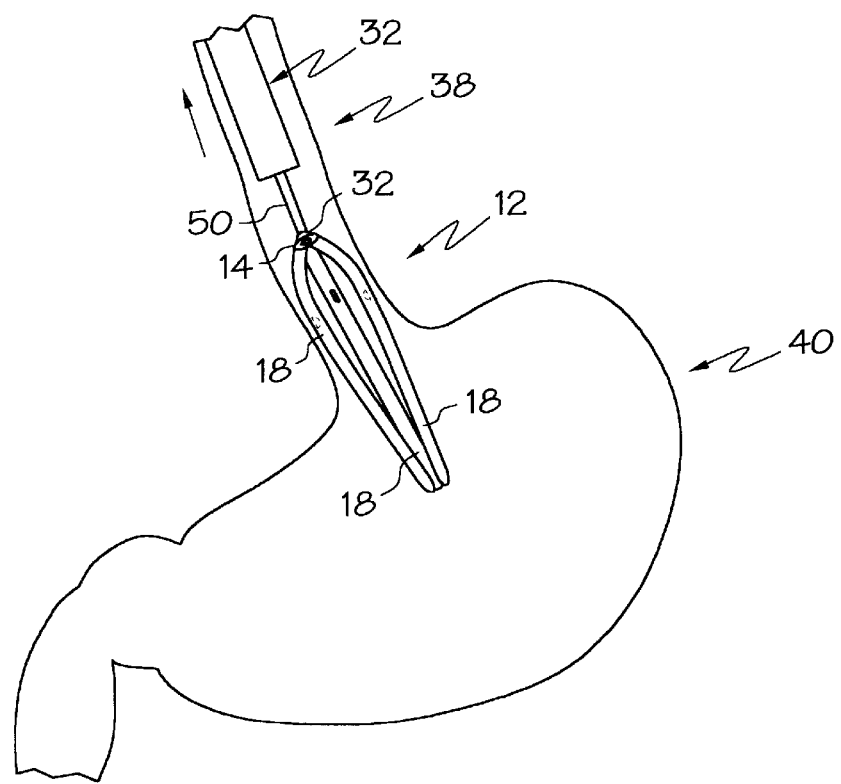
FIG. 11 shows the stomach insert being extracted out of the stomach and through the esophagus by the endoscopic forcep instrument in accordance with the extraction method of the present invention.

As shown in FIGS. 10 and 11, to remove the opened insert 12 back from the stomach 40 of the patient, the endoscope 32 is used to guide endoscopic forceps 50 the insert 12; and under endoscopic visualization, the forceps are used to grip the ring 32 projecting from the disc 14. Once sufficiently gripped by the forceps 50, because the blades are pivotally mounted to the disc and because the blades are sufficiently flexible, as the endoscope and forceps are pulled out through the esophagus and mouth, the insert 12 conforms to the narrowing size of the esophagus, allowing the instrument to be easily removed therefrom. Example forceps for use with the present invention include FB-22C-1/51253C triple-arm biopsy forceps, commercially available from Olympus Corp.

Of course it will be apparent to one of ordinary skill in the art that there are many types of endoscopic instruments and procedures which can be used to perform similar or identical steps as described above. Accordingly, the present invention provides a non-surgical (i.e., non-laproscopic) system and method for treating obesity in humans, and which also avoids many of the disadvantages and dangers of the prior art systems and methods for controlling appetite. Accordingly, having described the preferred embodiment of the invention in detail and by reference to the drawings, it will be apparent that modification and variations from the preferred embodiment are possible without departing from the scope of the invention as defined in the following claims.

What is claimed is:

1. An endoscopic stomach insert for treating obesity in humans by reducing the desire for eating, comprising:
    a base sized for passing through a human mouth and esophagus, said base having a central axis, an upper end and a lower end;
    a plurality of flexible spokes coupled at one end thereof to said base and circumferentially arranged about said axis, said spokes being biased to extend substantially radially outward from said base; and
    a retainer for releasably coupling distal portions of said spokes within close proximity to each other about said axis of said base;
    said spokes being of a sufficient length so as to be adapted to cause a sensation of fullness within a person's stomach after the insert is placed within stomach and the retainer is released.

2. The stomach insert of claim 1, wherein at least said distal portions of said spokes are also biased to extend downwardly below said lower end of said base.

3. The stomach insert of claim 1, wherein said base includes a guide-hole extending axially therethrough for receiving a guide-wire, whereby the base is adapted to ride on a guide-wire extending into a human mouth and esophagus and into the stomach, such that the insert can be easily deposited within the stomach using endoscopic procedures.

4. The stomach insert of claim 1, wherein said base is substantially disk-shaped, having a diameter ranging from approximately 6 millimeters to approximately 10 millimeters.

5. An endoscopic stomach insert for treating obesity in humans by reducing the desire for eating, comprising:
    a disk having a diameter sized for passing through a human mouth and esophagus, said disk further having a central axis, an upper end and a lower end, and said disk including a guide-hole extending axially therethrough for receiving a guide-wire;
    at least three flexible plastic blades, each of said blades having a longitudinal axis and each of said blades being substantially flat and curved with respect to said longitudinal axis, providing said blades with a concave surface and a convex surface, said blades having a proximate end and a substantially blunt distal end, and each of said blades being coupled at said proximate end to disk such that said concave surface faces downwardly, each of said blades including an eyelet extending from said concave surface at a point between said proximate end and said distal end, said blades being circumferentially arranged about said central axis of said disk, and said blades being biased to extend substantially radially outwardly and downwardly from said disk to form a substantially dome-shaped skeleton in an open position;
    a severable elastic band extending through each of said eyelets, coupling said blades within close proximity to each other, in a closed position, below said lower end of said disk, and about said central axis, to form a substantially asymmetrical elliptical skeleton; and
    a projection extending from an upper surface of said disk;
    whereby the disk is adapted to ride, in said closed position, on a guide-wire extending into a human mouth and esophagus and into the stomach, such that the insert can be deposited within the stomach;
    whereby, upon severing the band within the stomach, the blades will be biased to flare outwardly towards said open position, such that the convex surfaces of the blades will apply pressure to the stomach, thus causing a sensation of fullness within the stomach and reducing the desire for eating; and
    whereby the projection provides means for gripping the insert with an endoscopic instrument such that the insert can be extracted from the stomach, back through the esophagus, and out through the mouth.

6. An endoscopic stomach insert for treating obesity in humans by reducing the desire for eating, comprising:
    a base sized for passing through a human mouth and esophagus, said base having a central axis, an upper end and a lower end;
    a plurality of flexible spokes coupled at one end thereof to said base and circumferentially arranged about said axis, said spokes being biased to extend substantially radially outward from said base; and a retainer for releasably coupling distal portions of said spokes within close proximity to each other about said axis of said base;

wherein said plurality of spokes comprise at least three flexible blades, each of said blades having a longitudinal axis and each of said blades being substantially flat and curved with respect to said longitudinal axis, providing said blades with a concave surface and a convex surface, said blades having a proximate end and a substantially blunt distal end, and each of said blades being coupled at said proximate end to said base such that said concave surface faces downwardly;

whereby the insert is adapted to be passed through the mouth and esophagus and into a human stomach; and whereby, upon releasing the retainer within the stomach, the blades will be biased to flare outwardly such that said convex surfaces of the blades are thereby adapted to apply pressure to the stomach, thus causing a sensation of fullness within the stomach and reducing the desire for eating.

7. The stomach insert of claim 6, wherein said blades are plastic.

8. The stomach insert of claim 7, wherein:

each of said blades include an eyelet extending from said concave surface of said blade at a point between said proximate end and said distal end of said blade; and wherein said retainer includes a severable elastic band extending through each of said eyelets, coupling said blades within close proximity to each other below said lower end of said base, about said axis of said base.

9. The stomach insert of claim 8, wherein said blades are at least approximately 6 centimeters long.

10. An endoscopic stomach insert for treating obesity in humans by reducing the desire for eating, comprising:

a base sized for passing through a human mouth and esophagus, said base having a central axis, an upper end and a lower end;

a plurality of flexible spokes coupled at one end thereof to said base and circumferentially arranged about said axis, said spokes being biased to extend substantially radially outward from said base; and a retainer for releasably coupling distal portions of said spokes within close proximity to each other about said axis of said base;

each of said spokes including an eyelet extending from said spoke at a point distal from said base; and said retainer including a severable elastic band extending through each of said eyelets, coupling said spokes within close proximity to each other below said lower end of said base, about said axis of said base;

whereby the insert is adapted to be passed through the mouth and esophagus and into a human stomach; and whereby, upon severing said band within the stomach, the spokes will be biased to flare outwardly and are thereby adapted to apply pressure to the stomach, thus causing a sensation of fullness within the stomach, reducing the desire for eating.

11. An endoscopic stomach insert for treating obesity in humans by reducing the desire for eating, comprising:

a base sized for passing through a human mouth and esophagus, said base having a central axis, an upper end and a lower end;

at least three flexible spokes coupled at one end thereof to said base and circumferentially arranged about said axis, said spokes being biased to extend substantially radially outward from said base and said spokes being at least approximately 6 centimeters long; and a retainer for releasably coupling distal portions of said spokes within close proximity to each other about said axis of said base;

whereby the insert is adapted to be passed through the mouth and esophagus and into a human stomach; and whereby, upon releasing the retainer within the stomach, the spokes will flare outwardly and are thereby adapted to apply pressure to the stomach, thus causing a sensation of fullness within the stomach and reducing the desire for eating.

12. An endoscopic stomach insert for treating obesity in humans by reducing the desire for eating, comprising:

a base sized for passing through a human mouth and esophagus, said base having a central axis, an upper end and a lower end;

a plurality of flexible spokes coupled at one end thereof to said base and circumferentially arranged about said axis, said spokes being biased to extend substantially radially outward from said base;

a retainer for releasably coupling distal portions of said spokes within close proximity to each other about said axis of said base; and a projection extending from an upper surface of said base;

whereby the insert is adapted to be passed through the mouth and esophagus and into a human stomach;

whereby, upon releasing the retainer within the stomach, the spokes will flare outwardly and are thereby adapted to apply pressure to the stomach, thus causing a sensation of fullness within the stomach and reducing the desire for eating; and whereby the projection provides means for gripping the insert with an endoscopic instrument such that the insert can be extracted from the stomach, back through the esophagus, and out through the mouth.

13. An endoscopic stomach insert for treating obesity in humans by reducing the desire for eating, comprising:

a base sized for passing through a human mouth and esophagus, said base having a central axis, an upper end and a lower end;

a plurality of flexible spokes coupled at one end thereof to said base and circumferentially arranged about said axis, said spokes being biased to extend substantially radially outward from said base; and a retainer for releasably coupling distal portions of said spokes within close proximity to each other about said axis of said base, forming a substantially asymmetrical elliptical skeleton having a widest diameter that is at most approximately 2 centimeters;

whereby the insert is adapted to be passed through the mouth and esophagus and into a human stomach; and whereby, upon releasing the retainer within the stomach, the spokes will flare outwardly and are thereby adapted to apply pressure to the stomach, thus causing a sensation of fullness within the stomach and reducing the desire for eating.

14. An endoscopic procedure for treating obesity in humans by reducing the desire for eating comprising the steps of:

(a) endoscopically extending a guide-wire into a patient's mouth, through the patient's esophagus, and into the patient's stomach;

(b) guiding an endoscopic stomach insert along the guidewire, into the patient's mouth, through the patient's esophagus, and into the patient's stomach, the stomach insert including, a base sized for passing through the patient's mouth and esophagus, said base having a central axis, an upper end and a lower end;

a plurality of flexible spokes coupled at one end thereof to said base and circumferentially arranged about said axis, said spokes being biased to extend substantially radially outward from said base; and a retainer for releasably coupling distal portions of said spokes within close proximity to each other about said axis of said base to form a substantially elliptical cage having a widest diameter sized for passing through a patient's mouth and esophagus; and (c) endoscopically releasing the retainer such that the spokes will flare outwardly and apply pressure to the stomach, thus causing the patient to experience a sensation of fullness within the stomach and reducing the patient's desire for eating.

* * * * *